US006352833B1

(12) United States Patent
Mendelsohn

(10) Patent No.: US 6,352,833 B1
(45) Date of Patent: *Mar. 5, 2002

(54) METHODS FOR DISCOVERY OF VASOACTIVE COMPOUNDS FOR THE NITRIC OXIDE-CYCLIC GMP SIGNAL PATHWAY

(76) Inventor: Michael E. Mendelsohn, 14 Emerson Rd., Wellesley, MA (US) 02181

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/301,099

(22) Filed: Apr. 28, 1999

(51) Int. Cl.$^7$ .................. G01N 33/566; C12N 9/06; C12N 5/00; C12N 9/12; C07K 14/00

(52) U.S. Cl. .................. 435/7.2; 435/183; 435/194; 435/325; 530/350

(58) Field of Search .................. 530/350; 435/183; 435/194, 325, 7.2

(56) References Cited

U.S. PATENT DOCUMENTS 5,482,954 A * 1/1996 Kohn et al. .................. 514/359

OTHER PUBLICATIONS

Pfeifer et al. (1995) Cyclic GMP–dependent Protein Kinase Blocks Pertussis Toxin sensitive Hormone Receptor Signaling Pathways in Chinese Hamster Ovary Cells. J. Biol. Chem. 270(16)9052–9059.*
Wang et al. (1998) Mechanism of platelet inhibition by nitric oxide: In vivo phosphorylation of thromboxane receptor by cyclic GMP–dependent protein kinase. Proc. Natl. Acad. Sci. USA 95:4888–4893.*
Diviani et al. (1997) Characterization of the Phosphorylation Sites Involved in G protein–coupled Receptor Kinase— and Protein Kinase C–mediated Desensitization of the a1b–adrenergic receptor. J. Biol. Chem. 272(45):28712–28719.*
Geiger et al. (1992) Role of cGMP and cGMP–dependent protein kinase in nitrovasodilator inhibition of agonist–evoked calcium elevation in human platelets. Proc. Natl. Acad. Sci. USA (89):1031–1035.*
Hirata et al. (1990) Mechanism of Cyclic GMP Inhibition of Inositol Phosphate Formation in Rat Aorta Segments and Cultured Bovine Aortic Smooth Muscle Cells. J. Biol. Chem. 265(3)1268–1273.*
Kroner et al. (1996) Regulation of olfactory signalling via cGMP–dependent protein kinase. Eur. J. Biochem. 236, 632–637.*
Alessi et al., "The Control of Protein Phosphatase–1 by Targeting Subunits," *European Journal of Biochemistry*, 210: 1023–1035(1992).

Atkinson et al., "H NMR and Circular Dichroism Studies of the N–Terminal Domain of Cyclic GMP Dependent Protein Kinase: A Leucine/Isoleucine Zipper," *Biochemistry*, 30: 9387–9395 (1991).
Bradley et al., "Alterations in Cytoplasmic Calcium Sensitivity During Porcine Coronary Artery Contractions as Detected by Aequorin," *Journal of Physiology*, 385: 437–448 (1987).
Brautigan et al., "Methods to Distinguish Various Types of Protein Phosphatase Activity," *Methods in Enzymology*, 159: 339–346 (1988).
Cohen, "Classification of Protein–Serine/Threonine Phosphatases: Identification and Quantitation in Cell Extracts," *Methods in Enzymology*, 201: 389–390 (1991).
Cornwell et al., "Regulation of Intracellular $Ca^{2+}$Levels in Cultured Vascular Smooth Muscle Cells," *The Journal of Biological Chemistry*, 264: 1146–1155 (1989).
Gong et al., "Arachidonic Acid Inhibits Myosin Light Chain Phosphatase and Sensitizes Smooth Muscle to Calcium", *The Journal of Biological Chemistry*, 267: 21492–21498 (1992).
Harbury et al., "A Switch Between Two—, Three— and Four–Stranded Coiled Coils in GCN4 Leucine Zipper Mutants," *Science*, 262: 1401–1407(1993).
Hartshorne, "Biochemistry of the Contractile Process in Smooth Muscle," *Physiology of the Gastrointestinal Tract*, $2^{nd}$ Edition, 423–482 (1987).
Heil et al., "A Catalytically Active Fragment of cGMP–Dependent Protein Kinase," *European Journal of Biochemistry* 168: 117–121 (1987).
Hirano et al., "Interactions of the Subunits of Smooth Muscle Myosin Phosphatase," *The Journal of Biological Chemistry*, 6: 3683–3688 (1997).
Ishihara et al., "Calyculin A and Okadaic Acid: Inhibitors of Protein Phosphatase Activity," *Biochemical and Biophysical Research Communications*, 159: 871–877 (1989).
Johnson et al., "Identification of Protein–Phosphatase–1–Binding Domains on the Glycogen and Myofibrillar Targetting Subunits," *European Journal of Biochemistry*, 239: 317–325 (1996).
Kamm et al., "The Function of Myosin and Myosin Light Chain Kinase phosphorylation in Smooth Muscle," *Annual Review of Pharmacology and Toxicology*, 25: 593–620 (1985).

(List continued on next page.)

Primary Examiner—Prema Mertz
Assistant Examiner—Joseph F. Murphy
(74) Attorney, Agent, or Firm—Clark & Elbing LLP

(57) ABSTRACT

The invention features methods for assaying compounds that affect the activation of a cell. The methods include measurement of cell activation, G protein-coupled receptor phosphorylation, or phosphorylation of proteins associated with the G-protein-coupled receptor, in a system comprising G protein-coupled receptor-bearing cells, or preparations thereof, cyclic GMP, or analogs thereof, and cyclic GMP-dependent protein kinase.

11 Claims, 8 Drawing Sheets

OTHER PUBLICATIONS

Kimura et al., "Regulation of Myosin Phosphatase by Rho and Rho–Associated Kinase (Rho–Kinase)," *Science*, 273: 245–248 (1996).

Kitazawa et al., "G–Protein–Mediated $Ca^{2+}$ Sensitization of Smooth Muscle Contraction Through Myosin Light Chain Phosphorylation," *The Journal of Biological Chemistry*, 266: 1708–1715 (1991).

Landschulz et al., "The Leucine Zipper: A Hypothetical Structure Common to a New Class of DNA Binding Proteins," *Science*, 240: 1759–1764 (1988).

Lee et al., "Cyclic GMP Causes $Ca^{2+}$ Desensitization in Vascular Smooth Muscle by Activating the Myosin Light Chain Phosphatase," *The Journal of Biological Chemistry*, 272: 5063–5068 (1997).

Lincoln et al., "Purification and Subunit Composition of Guanosine 3':5'–Monophosphate–dependent Protein Kinase from Bovine Lung," *The Journal of Biological Chemistry*, 252: 4269–4275 (1977).

Lincoln et al., "Intracellular Cyclic GMP Receptor Proteins," *The FASEB Journal*, 7, pp. 328–338 (1993).

Lincoln, "Cyclic GMP and Vascular Biology," *Biochemistry, Physiology and Pathophysiology*, R.G. Landes Company, Austin, Chapter 7, 97–132 (1994).

Lohmann et al., "Distinct and Specific Functions of cGMP–Dependent Protein Kinases," *Trends in Biological Science* 22: 307–312 (1997).

Masuo et al., "A Novel Mechanism for the $Ca^{2+}$–Sensitizing Effect of Protein Kinase C on Vascular Smooth Muscle: Inhibition of Myosin Light Chain Phosphatase," *Journal of General Physiology*, 104: 265–286 (1994).

Monken et al., "Structural Analysis of cGMP–Dependent Protein Kinase Using Limited Proteolysis," *The Journal of Biological Chemistry*, 255: 7067–7070 (1980).

Pfeifer et al., "Defective Smooth Muscle Regulation in cGMP Kinase I–Deficient Mice," *The EMBO Journal*, 17: 3045–3051 (1998).

Shimizu et al., "Characterization of the Myosin–binding Subunit of Smooth Muscle Myosin Phosphatase," *The Journal of Biological Chemistry*, 269: 30407–30411 (1994).

Somlyo et al., "Signal Transduction and Regulation in Smooth Muscle," *Nature*, 372: 231–236 (1994).

Tamura et al., "cDNA Cloning and Gene Expression of Human Type 1α cGMP–Dependent Protein Kinase," *Hypertension*, 27:552–557 (1996).

Turner et al., "Leucine Repeats and an Adjacent DNA Binding Domain Mediate the Formation of Function cFos–cJun Heterodimers," *Science*, 243: 1689–1694 (1989).

Wu et al., "Cyclic GMP–Dependent Stimulation Reverses G–Protein–Coupled Inhibition of Smooth Muscle Myosin Light Chain Phosphatase," *Biochemical and Biophysical Research Communications*, 220: 658–663 (1996).

* cited by examiner

METHODS FOR DISCOVERY OF VASOACTIVE COMPOUNDS FOR THE NITRIC OXIDE-CYCLIC GMP SIGNAL PATHWAY

STATEMENT AS TO FEDERALLY SPONSORED RESEARCH

The invention was made with funding from the National Institutes of Health, grants HL36838 and HL55309. The government has certain rights in the invention.

FIELD OF THE INVENTION

The invention relates to methods useful for delaying or ameliorating human diseases associated with endothelial dysfunction.

BACKGROUND OF THE INVENTION

The vascular endothelium plays a critical regulatory role due to its physical location between circulating blood and vascular smooth muscle cells. In response to mechanical and hormonal signals from the blood, endothelial cells release substances which modulate platelet adhesion and aggregation and affect contraction and proliferation of vascular smooth muscle.

Under physiological conditions, the endothelium maintains the vasculature in a dilated state, inhibits vascular smooth muscle proliferation, and prevents the adhesion of circulating platelets and monocytes. Thus, the endothelium modulates the tone of the underlying vascular smooth muscle.

Activation or injury to the endothelium leads to the development of endothelial dysfunction which contributes to adhesion and aggregation of platelets, vasoconstriction, and proliferation of vascular smooth muscle cells. Endothelial dysfunction is present in a variety of conditions associated with aging, diabetes, gastrointestinal disease, hyperglycemia, hypercholesterolemia, peripheral vascular disease, stroke, hypertension, thrombosis, angina, atherosclerosis and other cardiovascular diseases.

In view of the wide range of disorders that are associated with endothelial dysfunction, it would be desirable to identify compounds that are capable of enhancing the effects of endothelial-derived substances on their target cells, including vascular smooth muscle cells and platelets.

SUMMARY OF THE INVENTION

Here we present evidence that G protein-coupled receptors are regulated by cyclic GMP-dependent protein kinase (G kinase), the principle mediator of nitric oxide-cyclic GMP (NO-cGMP) signaling which modulates inhibition of platelet aggregation and relaxation of vascular smooth muscle. The invention provides methods for identifying compounds which mimic the effects of NO-cGMP on platelets and vascular smooth muscle cells to enhance platelet inhibition and vascular smooth muscle cell relaxation.

In the first aspect, the invention features a method of assaying a test compound, the method comprising: providing a system comprising a G protein-coupled receptor-bearing cell, cyclic GMP or an analog thereof, and cyclic GMP-dependent protein kinase; contacting the test compound with the system; and determining whether the test compound affects either the activation of the cell or the phosphorylation of the G-protein-coupled receptor or fragment thereof, or the phosphorylation of proteins associated with the G-protein-coupled receptor. In a preferred embodiment of this aspect, the cell is selected from the group consisting of platelets, human erythroleukemia (HEL) cells, and vascular smooth muscle cells. Alternatively, the cell may be genetically engineered to express the G protein-coupled receptor or fragment thereof. In other embodiments of this aspect, determining whether the test compound affects either the activation of the cell or the phosphorylation of the G-protein-coupled receptor or fragment thereof, or the phosphorylation of proteins associated with the G-protein-coupled receptor may be done in vitro or in vivo A second aspect of the invention provides a method of assaying a test compound, the method comprising: providing a system comprising a G protein-coupled receptor-bearing cell preparation, cyclic GMP or an analog thereof, and cyclic GMP-dependent protein kinase; contacting the test compound with the system; and determining whether the test compound affects either the activation of the cell or the phosphorylation of the G-protein-coupled receptor or fragment thereof, or the activation or phosphorylation of proteins associated with the G-protein-coupled receptor. In a preferred embodiment of this aspect, the cell preparation is made from cells selected from the group consisting of platelets, HEL cells, and vascular smooth muscle cells.

In other preferred embodiments of the invention, the method further comprises a G protein-coupled receptor agonist and may include measuring GTPase activity. In another preferred embodiment of the invention, the G-protein-coupled receptor may be selected from the group consisting of the thromboxane receptors, thrombin receptors, serotonin receptors, purinergic receptors, adrenergic receptors, bradykinin receptors, angiotensin receptors, cAMP receptors, dopamine receptors, muscarinic receptors, opioid receptors, opsin receptors, and isoforms thereof.

By "test compound" is meant any chemical compound, be it naturally-occurring or artificially-derived. Test compounds may include, for example, peptides, polypeptides, synthesized organic molecules, naturally occurring organic molecules, and nucleic acid molecules.

By "contacting" is meant to submit an animal, cell, lysate, or extract derived from a cell, or molecule derived from a cell to a test compound.

By "cell preparation" is meant an extract or lysate of a cell or a component thereof.

By "affects" is meant changes, either by increase or decrease.

By "determining" is meant analyzing the effect of a test compound on the test system. The readout of the analysis may be altered protein stability, levels, or biological activity. The means for analyzing may include, for example, antibody labeling, immunoprecipitation, in vivo and in vitro phosphorylation assays, protease or glucosidase digestion, GTPase assays, measures of inositol triphosphate production, intracellular calcium mobilization, and other methods known to those skilled in the art.

By "G protein-coupled receptor" is meant a receptor with seven transmembrane domains which uses a heterotrimeric G protein as an intermediary in signal transduction. G protein-coupled receptors belong to a large superfamily of receptors that share a structural motif of seven transmembrane helices. G protein-coupled receptors include adrenergic, angiotensin, cAMP, dopamine, muscarinic, opioid, opsins, purinergic, serotonin, thrombin, thromboxane, and isoforms thereof, or any other G protein-coupled receptors that are known to couple with G proteins.

By "activation" is meant the response of a cell to a substance, whether endogenously derived or exogenously administered. The response may include changes in shape (for example, contraction), aggregation, intracellular calcium mobilization, inositol triphosphate production, expression of cell surface activation markers, increase in cell proliferation markers, increases in gene expression, and other features known to those skilled in the art.

By "proteins associated with the G protein-coupled receptor" is meant any protein or peptide that forms a complex with the G protein-coupled receptor by means of covalent, non-covalent, reversible, or other form of protein-protein interaction known to those skilled in the art.

The invention provides a means of identifying test compounds that affect vascular smooth muscle relaxation, inhibition of platelet activation, or other markers of endothelial dysfunction. This is particularly useful because endothelial dysfunction has been correlated with a variety of conditions associated with aging, diabetes, gastrointestinal disease, hyperglycemia, hypercholesterolemia, peripheral vascular disease, stroke, hypertension, thrombosis, angina, atherosclerosis and other cardiovascular diseases. Thus, compounds that affect endothelial dysfunction may be used in therapy or diagnosis of such diseases.

Other features and advantages of the invention will be apparent from the following detailed description, and from the claims.

DETAILED DESCRIPTION OF THE INVENTION

Figure 1A:
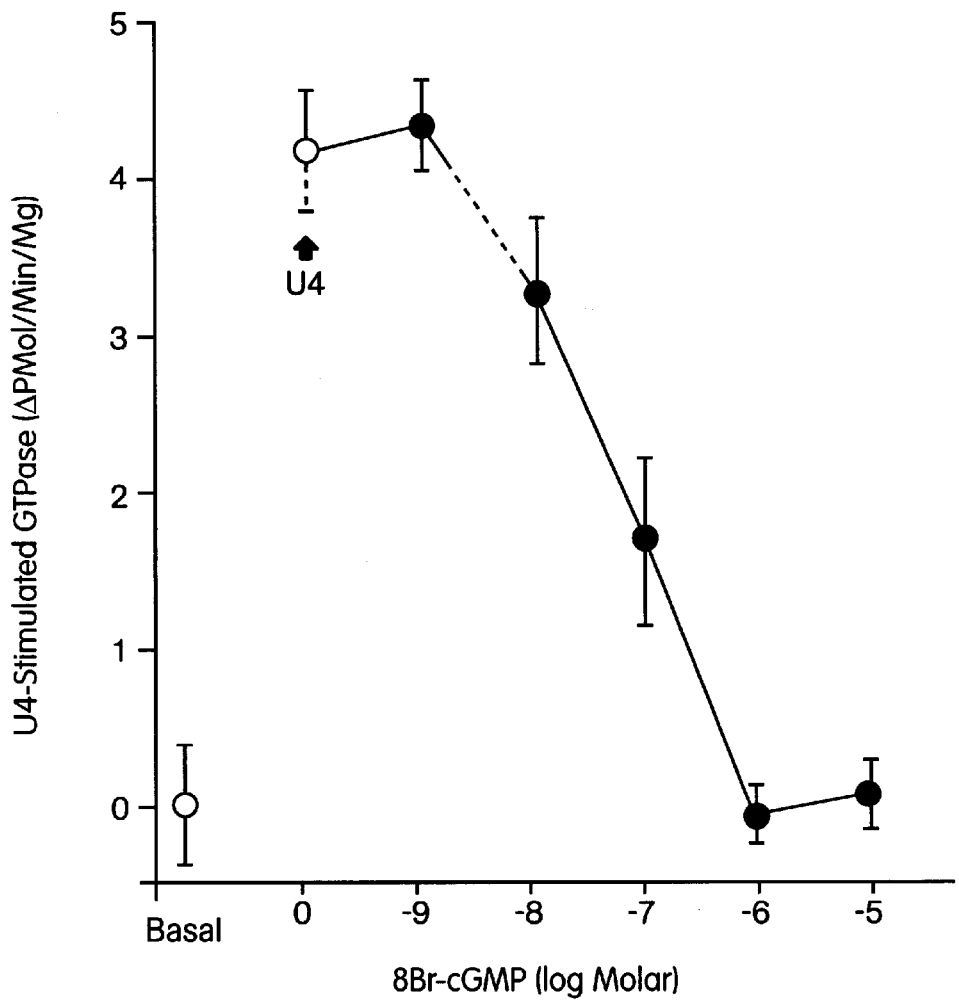
FIG. 1A is a graph showing the inhibition of $TXA_2$ receptor-coupled GTPase activation in human platelet membranes by 8-Br-cGMP.

The vascular endothelium generates nitric oxide (NO), the most important endogenous vasoactive compound known to date. Decreases in the NO system are associated with increased platelet activation, increased vasoconstriction, and altered vascular tone and structure.

NO mediates the relaxation of vascular smooth muscle cells and inhibition of platelet aggregation, stimulating the production of cyclic GMP (cGMP). The effects of cGMP are principally mediated by cGMP-dependent protein kinase (G kinase) which mobilizes intracellular calcium through a variety of processes, including phospholipase C activation and inositol triphosphate generation.

G protein-coupled receptors belong to a superfamily of receptors that share a structural motif of seven transmembrane domains. These receptors are activated by the binding of their cognate ligands (or agonists), initiating signal transduction through an intermediary heterotrimeric GTP binding protein (G protein) and activating second messenger systems.

Binding of a G protein-coupled receptor to a heterotrimeric G protein generally occurs through the cytoplasmic receptor domains, especially the third intracellular loop and the cytoplasmic carboxyl-terminal tail. The receptor-G protein interaction can be uncoupled by phosphorylation of the receptor, which is the principle mechanism by which this family of receptors is rapidly desensitized following agonist activation.

Agonist activation of G protein-coupled receptors is tightly and reciprocally regulated by two types of kinases: G protein receptor kinases (GRK) and second messenger kinases. GRK, such as rhodopsin kinase and the β-adrenergic receptor kinases, desensitize active receptors only after agonist stimulation, which initiates GRK recruitment and receptor phosphorylation. Cyclic AMP-dependent protein kinase and protein kinase C also have been reported to catalyze the phosphorylation and promote the desensitization of the β-adrenergic and other receptors following agonist activation in vitro.

We have discovered that G protein-coupled receptors are regulated by G kinase, the principle mediator of NO-cGMP signaling, in a manner distinct from regulation by GRK and other kinases. We conclude from our observations that this regulation may be used to identify compounds that modulate endothelial cell function, in particular the inhibition of platelet activation.

Assay

G protein-coupled receptor-bearing cells may be obtained as follows. Platelets may be obtained from outdates (Blood Bank). Vascular smooth muscle cells, HEL cells, and other cells may be obtained from ATCC. Alternatively, G protein-coupled receptor DNA may be obtained from various sources and introduced into suitable cells, for example, COS7 or HEK293 cells, by standard transfection techniques.

The levels of G protein-coupled receptors may be ascertained by standard assays such as immunoblotting or immunoprecipitation. Endogenous G protein-coupled receptors may be distinguished from the introduced receptors by, for example, epitope tagging the introduced receptor with myc or HA tags.

Cyclic GMP or analogs of cGMP, such as 8-Bromo-cyclic GMP, may be used at concentrations known to activate G protein-coupled receptor-bearing cells. Cyclic GMP-dependent protein kinase may be obtained from Promega, Madison, Wis. Concentrations of the test compounds may be approximately $10^{-12}$–$10^{-5}$ M.

Activation of the cell (platelet, vascular smooth muscle cell, or other cell type) may be measured by the measurement of shape change (for example, contraction), aggregation, intracellular calcium mobilization, inositol triphosphate production, expression of cell surface activation markers, increase in cell proliferation markers, increases in gene expression, or other techniques known to those skilled in the art. Phosphorylation of the G protein-coupled receptor may be measured by incorporation of $^{32}P$, in vivo or in vitro, and either radioisotope counting or autoradiographic methods.

The following examples are to illustrate the invention. They are not meant to limit the invention in any way.

EXAMPLE 1

Inhibition of $TXA_2$ Receptor-Coupled GTPase Activation by 8-Bromo-Cyclic GMP

Treatment of platelets with NO or cGMP inhibits the ability of several agonists to stimulate phospholipase C, generate inositol triphosphate, and mobilize intracellular calcium (Mendelsohn, M. E. et al., 1990, *J. Biol. Chem.* 265: 19028–19034; Takai, Y. et al., 1981, *Biochem. Biophys. Res. Commun.* 101: 61–67; Nakashima, S. et al., 1986, *Biochem. Biophys. Res. Commun.* 135: 1099–1104; Ruth, P. et al., 1993, *Proc. Natl. Acad. USA* 90: 2623–2627; Kroll, M. H., 1994, in *Thrombosis and Hemorrhage*, Eds. Loscalzo, J. & Schafer, A. I., Blackwell Scientific, Oxford, Vol. 13, pp. 247–277).

The arachidonic acid metabolite thromboxane $A_2$ ($TXA_2$) stimulates platelet aggregation and regulates vascular smooth muscle cell contraction by binding to a G protein-coupled receptor, the $TXA_2$ receptor. Inhibitors of $TXA_2$ production decrease ischemic events in clinical populations (Cairns, J. A., 1987, *Cardiovasc. Clin.* 18:231–246), supporting an important role for $TXA_2$ in physiological regulation of hemostasis and thrombosis. The signal transduction events initiated by $TXA_2$ stimulation of platelets are well characterized. $TXA_2$ receptor isoforms cause platelet activation by increasing phosphoinositide-specific phospholipase C (PLC) activity through the pertussis-insensitive GTP binding protein, $G\alpha_q$, PLC generates inositol triphosphate, leading to the release of intracellular calcium and activation of $Ca^{2+}$/calmodulin-regulated proteins such as myosin light chain kinase. Myosin light chain kinase then phosphorylates myosin light chain, promoting platelet aggregation and granule secretion (reviewed in Kroll, M. H., supra).

To demonstrate that cGMP can directly influence receptor-G protein coupling, the effect of the nonhydrolyzable cGMP derivative, 8-bromo-cyclic GMP (8-Br-cGMP), on the $TXA_2$-specific GTPase in human platelet membranes was studied. Platelets were prepared from plateletpheresis units as described (Benka, M. L. et al., 1995, supra; Zhu, Y. et al., 1994, supra).

$TXA_2$-stimulated GTPase activity was measured in platelet membranes by initiating reactions by the addition of 20–45 μg of platelet membranes to tubes in the absence or presence of 10 μM of the thromboxane analog, U46619, (Benka, M. L. et al., The MBL Physiology Course, Busa, W. B. & Mendelsohn, M. E., 1995, *FEBS Lett.* 363: 49–52). The final reaction mixture (total volume=100 μl) contained 0.4 μM GTP, including 0.6–0.9 μCi of [γ-$^{32}P$]GTP(1.5–2×10$^6$ dpm), as well as 100 mM NaCl, 0.1 mM EGTA, 2 mM $MgCl_2$, 1 mM dithiothreitol, 0.1 mM ATP, 5 mM phosphocreatine, 100 units/ml creatine phosphokinase, 0.2% bovine serum albumin, 50 mM triethanolamine HCl, pH 7.4, and indicated concentrations of agonist.

For experiments with 8-Br-cGMP, platelet membranes were incubated at room temperature for 10 minutes in 8-Br-cGMP (1 nM to 100 μM) prior to stimulation with U46619. GTPase reactions were terminated with 5% activated charcoal/20 mM phosphoric acid, and high affinity GTPase activity was measured and calculated (Shenker, A. et al., 1991, *J. Biol. Chem.* 268: 26011–26017; Benka et al., supra).

In untreated membranes, U46619 caused the expected stimulation of $TXA_2$-specific GTPase activity (Shenker, A. et al., supra; Albers, F. J. et al., 1992, *Naunyn-Schmiedeberg's Arch. Pharmacol.* 346: 127–137), with an average increase in GTPase activity of 5.5±1.3 pmol of $^{32}P$/min/mg platelet protein (n=three experiments in triplicate). The effects of cyclic GMP on this $TXA_2$-specific GTPase were studied next by pretreating the platelet membranes with 8-Br-cGMP. FIG. 1A shows basal GTPase activity (open circle), U46619-stimulated activity in buffer-treated membranes (grey circle: ↑U4), and the progressive inhibition of U46619-stimulated GTPase by 8-Br-cGMP (dark circles). Thus, pretreatment of the platelet membranes with 8-Br-cGMP inhibited the U46619-stimulated GTPase activity in a dose-dependent fashion (mean $IC_{50}$=75 nm; n=3 experiments in triplicate). In separate studies, pretreatment of platelet membranes with 500 μm 8-Br-cGMP only minimally decreased basal platelet membrane GTPase activity (by 8±9%, n=4).

Figure 1B:
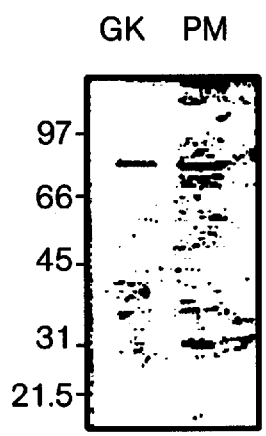
FIG. 1B is an immunoblot showing G kinase in human platelet membranes.

Immunoblotting studies of the platelet membranes used in these studies demonstrated high levels of G kinase (FIG. 1B) where lane 1 (GK) contains 0.2 μg of purified G kinase and lane 2 (PM) contains 79 μg of total platelet membrane protein.

In addition, the half-maximal concentration of 8-Br-cGMP necessary for GTPase inhibition in these studies was very similar to the $K_{Act}$ for G kinase (Lincoln, T. M. et al., 1983, *Adv Cyclic Nucleotide Res.* 15, 192). This indicated that the observed uncoupling of receptor GTPase activation was due to the action of G kinase on substrates, such as the G protein-coupled receptors.

EXAMPLE 2

Phosphorylation of the $TXA_2$ Receptors by G kinase

To demonstrate that the $TXA_2$ receptors themselves were substrates for G kinase, an antibody (TXR2) was raised against the $TXA_2$ receptor. The antibody was raised in rabbits using a glutathione-S-transferase (GST) fusion peptide based on the third cytoplasmic loop of the $TXA_2$ receptor (amino acids 221-TLCHVYHGQEAAQQRPRDSEVEMMAQ-246). The GST-fusion protein was generated by in-frame ligation of the cDNA corresponding to the third intracytoplasmic domain of the receptor to the expression plasmid pGEX3X, as reported previously (Zhu, Y. et al., 1994, *J. Biol. Chem.* 269: 22379–22384).

Antisera were screened by dot-blotting methods using the GST-peptide antigen, with GST alone used as control (Harlow, E. et al., 1988, *Antibodies: A Laboratory Manual*, Cold Spring Harbor Lab. Press, Plainview, N.Y., pp. 1–726). Peptide antisera TXR2 specifically recognized the intracytoplasmic loop 3 peptide and also recognized a 48–53 kDa protein in human platelets corresponding to the endogenous $TXA_2$ receptor (FIG. 2).

Platelet lysis conditions with varying detergent and ionic conditions were optimized to maximize recovery of the $TXA_2$ receptors. The radioimmunoprecipitation buffer chosen for all experiments consisted of 25 mM Tris-HCl, pH 7.8, 5 mM MgCl$_2$, 2.5 mM EDTA, 0.5% digitonin, with a mixture of protease inhibitors (1 mM phenylmethylsulfonyl fluoride, 100 ng/ml chymostatin, 2 ng.ml aprotinin, 1 μg/ml E-64, 0.5 μg/ml leupeptin, 2.5 μg/ml antipain, 100 μM benzamidine). Platelet lysates were precleared with protein A beads prior to the receptor isolation experiments to remove any potential residual human IgG.

To isolate TXA$_2$ receptors free from the TXR2 antibody IgG heavy chain, TXR2 antibody was covalently coupled to agarose beads and used to immunopurify native TXA$_2$ receptor from concentrated human platelet lysates. The TXR2 antibody was first purified and concentrated on protein A beads, eluted with 100 mM glycine, pH 3.0, adjusted to pH 7.0, and then covalently linked to Sulfolink coupling gel beads (Pierce, Rockford, Ill.). Antibody beads were next washed, mixed with 2 ml on concentrated platelet lysate (from≈10$^{10}$ platelets), incubated for 3 hours with rocking, and then washed extensively with radioimmunoprecipitation buffer. Receptors were eluted with 100 mM glycine buffer, pH 3.0, as described (Harlow et al., 1988, supra).

All immunoblotting studies were performed as described previously and developed using the enhanced chemiluminescence system (Amersham, Piscataway, N.J.) (Mendelsohn, M. E. et al., 1991, Proc. Natl. Acad. Sci. USA 88: 11212–11216). In some experiments, membranes were stripped with 100 mM β-mercaptoethanol, 2% SDS, 62.5 mM Tris-HCl, pH 6.8, at 50° C. for 30 minutes, blocked and reprobed with a different antibody.

Figure 2A:
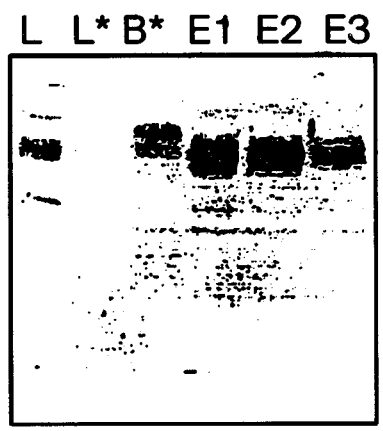
FIG. 2A is an immunoblot demonstrating immunoaffinity isolation of $TXA_2$ receptors.

FIG. 2A demonstrates the immunoaffinity isolation of TXA$_2$ receptors from human platelet lysates. The lanes in FIG. 2A contain the following: L, platelet lysate; L*, lysate after incubating with TXR2 antibody beads; B*, IgG from TXR2 beads, E1–E3, sequential eluates from the TXR2 antibody beads incubated with platelet lysate, washed and then eluted with low pH glycine buffer. The 47–53 kDa band in lanes L, E1, E2, and E3 is the platelet TXA$_2$ receptor. Therefore, the eluted TXA$_2$ receptor migrated with an M$_r$ of 48–53 kDa, was recognized by the TXR2 antibody on immunoblots, and migrated just below and entirely free from any IgG heavy chain.

Peptide mapping studies of immunopurified TXA$_2$ receptors were undertaken next with endoproteinase Lys-C, which cleaves and releases the seventh transmembrane domain and cytoplasmic tail of TXA$_2$ receptors from the main body of the receptor by proteolysis of Lys-288. Enzymatic proteolysis was performed by the method of True and Mais (True, T. A. et al., 1994, Eur. J Pharmacol. 266:51–55) using enzyme conditions recommended by the manufacturer (Boehringer Mannheim). Deglycosylation of the receptors was performed using N-glucosidase F (Boehringer Mannheim).

Figure 2B:
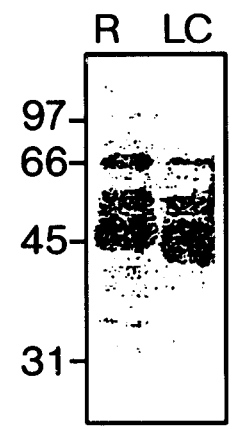
FIG. 2B is an immunoblot showing endoproteinase Lys-C digestion of immunopurified $TXA_2$ receptors.

Endoproteinase Lys-C digestion of the immunopurified receptor protein led to the expected decrease in receptor M$_r$ due to release of the C-terminal domain of the TXA$_2$ receptor. Digestion of the TXA$_2$ receptor with N-glucosidase F also gave the expected decrease in receptor M$_r$ due to deglycosylation, as described previously (True, T. A. et al., 1994, supra; Mais, D. E. et al., 1992, Eur. J. Pharmacol. 227:267–274). FIG. 2B shows one of four similar experiments demonstrating the expected decrease in M$_r$ of the TXA$_2$ receptor following endoproteinase Lys-C digestion where lane R shows immunopurified TXA$_2$ receptors and LC shows TXA$_2$ receptors digested with endoproteinase Lys-C.

In separate immunoprecipitation experiments, we also examined whether Gα$_q$/Gα$_{11}$ or its effector PLCβ, were phosphorylated in response to NO or cGMP. Anti-Gα$_q$/Gα$_{11}$ antibodies were obtained from D. Manning (University of Pennsylvania; Woolkalis, M. J. et al., 1986, J. Biol. Chem. 261:3408–3413). Immunoprecipitation of Gα$_q$/Gα$_{11}$ from $^{32}$P-labeled platelets treated with buffer alone, S-nitrosothiol, S-nitroso-N-acetylcysteine, or 8-Br-cGMP did not demonstrate any significant G protein phosphorylation. Similarly, in studies using a variety of different monoclonal and polyclonal PLCβ antibodies, no increase in phosphorylation of PLCβ due to NO or cGMP was detected.

TXA$_2$ receptor eluates were introduced into kinase reactions with purified G kinase (29–145 nM), which demonstrated in vitro phosphorylation of TXA$_2$ receptors. Interestingly, and as observed previously, Gα$_q$/Gα$_{11}$ G proteins copurified with the TXA$_2$ receptors in these experiments but were not phosphorylated in any of the in vitro G kinase reactions. The G kinase antibody, RIFB, was immunopurified and has been described in detail (Lincoln, T. M. et al., 1989, Am. J Physiol., 399–407).

To examine whether cGMP can lead to phosphorylation of TXA$_2$ receptors in vivo, studies were performed using HEL cells, which contain high densities of the platelet TXA$_2$ receptor (Allan, C. J. et al., 1996, J. Pharmacol. Exp. Ther. 277:1132–1139; Mayeux, P. R. et al., 1989, J. Pharmacol. Exp. Ther. 250:923–927).

HEL cells were labeled with $^{32}$P (Mendelsohn, M. E. et al., 1991, supra) and then exposed to buffer alone (10 minutes), U46619 (5 μM, 10 minutes), or 8-Br-cGMP (10 mM, 15 minutes). Reactions were terminated by addition of ice-cold TEB buffer: 20 mM Tris-Cl, pH 7.4, 5 mM EGTA, 0.128 mg/ml phenylmethylsulfonyl fluoride, 0.15 mg/ml benzamidine Cl, followed by preparation of solubilized TXA$_2$ receptor fractions in CHAPS buffer: 20 mM Tris-Cl, pH 7.4, 5 mM EGTA, 25% glycerol, 0.128 mg/ml phenylmethylsulfonyl fluoride, 0.15 mg/ml benzamidine Cl, 10 mM CHAPS (Schror, K. et al., 1995, Biochem. Pharmacol. 49: 921–927). TXA$_2$ receptor fractions were then purified on and eluted from TXA$_2$ antibody affinity beads, resolved by SDS-PAGE, and transferred to nitrocellulose. Receptor was quantified by immunoblotting and phosphorylation was quantitated by PhosphorImager analysis (Mendelsohn, M. E. et al., 1991, supra). For peptide mapping of in vivo phosphorylated TXA$_2$ receptors with endoproteinase Lys-C, receptor bands were excised from the nitrocellulose and eluted overnight in elution buffer: 50 mM Tris-Cl, pH 9.0, 2% SDS, and 1% Triton-X-100 (Harrington, M. G., 1990, ed. Deutscher, M. P. pp 488–495). Eluates were then dialyzed for 48 hours against 25 mM Tris-CL, pH 8.5, 1 mM EDTA, subjected to enzymatic proteolysis, and resolved on 15% SDS/PAGE gels.

Figure 3A:
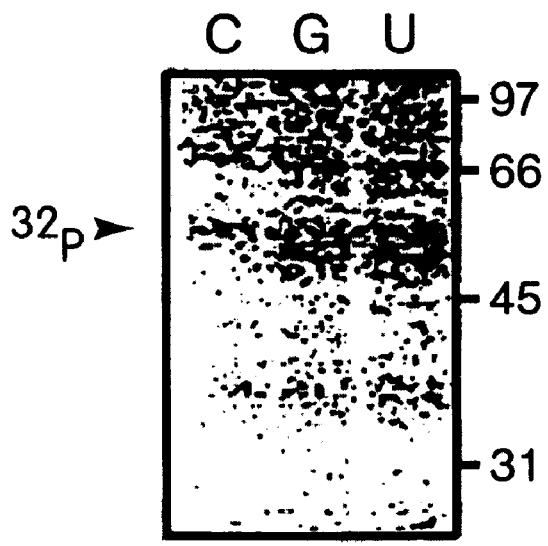
FIG. 3A is an autoradiograph showing immunopurified $TXA_2$ receptor.
Figure 3B:
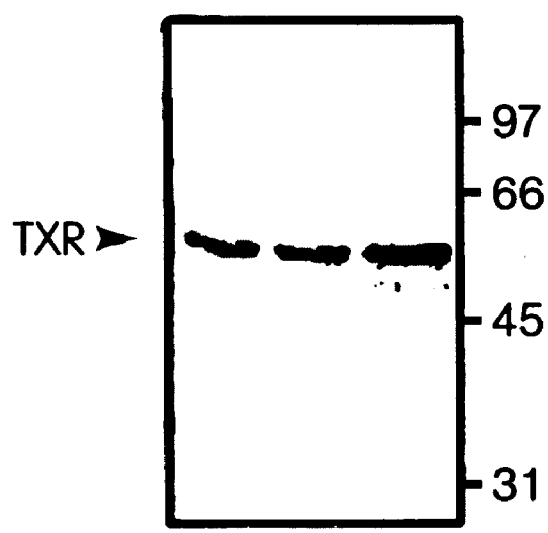
FIG. 3B is an immunoblot showing immunopurified $TXA_2$ receptor.

FIG. 3A shows one of five similar experiments demonstrating in vivo phosphorylation of immunopurified TXA$_2$ receptor by cyclic GMP and the thromboxane analog U46619. The lanes are as follows: C, vehicle control, 10 minutes; G, 10 mM 8-Br-cGMP, 15 minutes; U, 5 μM U46619, 10 minutes. TXA$_2$ receptors were isolated by immunoaffinity methods from $^{32}$P-labeled HEL cells, resolved by SDS/PAGE, transferred to nitrocellulose, and subjected to autoradiography and immunoblotting. FIG. 3B is an TXR2 antibody immunoblot of the autoradiograph in FIG. 3A. As expected, TXA$_2$ receptors in these experiments were phosphorylated following treatment of $^{32}$P-labeled cells with the thromboxane analog, U46619, due to agonist-mediated activation of G protein receptor kinase(s) (Lefkowitz, 1993, Cell 74:409–412; FIG. 3A, lane U). 8-Br-cGMP treatment also led to clear and significant increases in TXA$_2$ receptor phosphorylation to a level comparable with agonist-induced phosphorylation (FIG. 3A, lane G).

Figure 4:
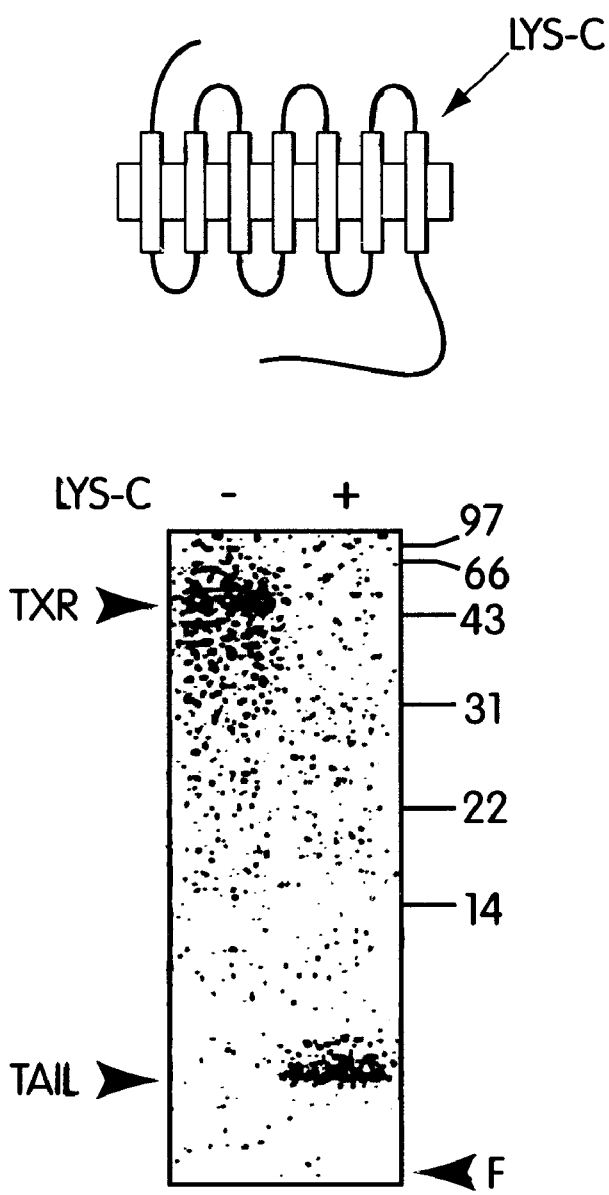
FIG. 4 is an autoradiograph showing endoproteinase Lys-C digestion of in vivo phosphorylated $TXA_2$ receptors.

FIG. 4 shows one of two similar experiments demonstrating endoproteinase Lys-C digestion of in vivo phosphorylated TXA$_2$ receptors. Undigested in vivo phosphorylated TXA$_2$ receptors (−) or receptors enzymatically digested by endoproteinase Lys-C (+) were resolved by 15% SDS/PAGE. The results were identical to Lys-C digestion of immunopurified TXA$_2$ receptors phosphorylated in vitro. Digestion of in vivo phosphorylated TXA$_2$ receptors with endoproteinase Lys-C resulted in the release of receptor-associated $^{32}$P into a small 6–8 kDa carboxyl-terminal tail fragment of the receptor ("tail"). "F" refers to the gel front. Little or no phosphorylation was seen associated with any larger Mr proteins following endoproteinase Lys-C digestion in these studies (FIG. 4). These data point to the G kinase phosphorylation site(s) as somewhere distal to Lysine 288 in the carboxyl terminus of the TXA$_2$ receptor.

EXAMPLE 3

Phosphorylation of the TXA$_2$ Receptor Cytoplasmic Terminal Peptide by G Kinase The third intracytoplasmic loop and the cytoplasmic tails of both the TXA$_2$ receptors, α and β all contain potential serine/threonine phosphorylation sites for G kinase, with 2, 6, and 17 serine/threonine residues, respectively.

Figure 5A:
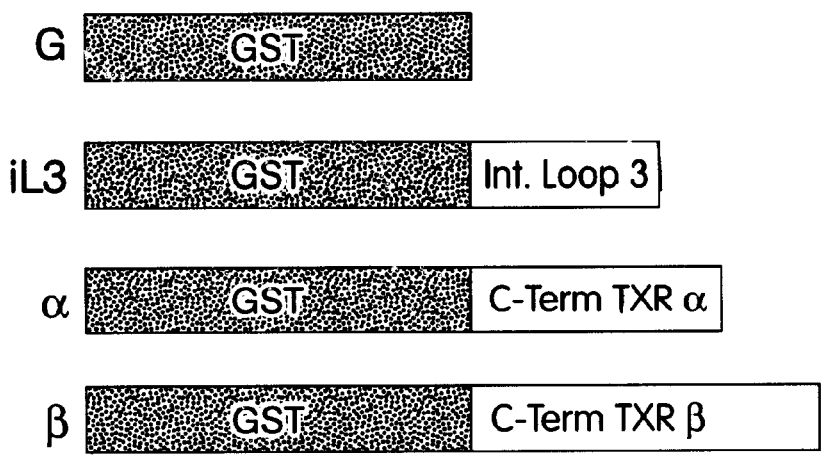
FIG. 5A is a schematic representation of GST-fusion peptides.

To examine further the potential phosphorylation of cytoplasmic domains of TXA$_2$ receptors, an in vitro phosphorylation assay was used to test the ability of G kinase to catalyze the phosphorylation of GST-fusion proteins derived from the third intracytoplasmic loop and C-terminal domains of the TXA$_2$ receptors (FIG. 5A).

In vitro phosphorylation experiments with immunopurified TXA$_2$ receptors were performed (Cornwell, T. L. et al., 1989, *J. Biol. Chem.* 264:1146–1155; Lincoln, T. M. et al., 1996, *Methods Enzymol.* 269:149–166). Reactions were in 50 mM Tris-HCl, pH 7.5, 5 mM MgCl$_2$, 0.1 mM cGMP for 10–15 minutes at room temperature and were initiated by addition of 10 μCi of [γ-$^{32}$P]ATP (6,000 Ci/mmol; Dupont,/NEN) and stopped by addition of HCl to a final concentration of 10 mM. GST-fusion peptides were prepared from the full-length TXA$_2$ receptor cDNA as template in PCR reactions in which cDNAs corresponding to the third intracytoplasmic loop and the cytoplasmic tails of the TXA$_2$ receptors were amplified. The sequences amplified for each construct corresponds to the third intracytoplasmic loop (iL3) amino acids 220–246; for the TXA$_2$ receptor α C terminus, amino acids 310–343; and for the TXA$_2$ receptor β C terminus, amino acids 310–369. All cDNA were subcloned into the GST-fusion protein expression vector pGEX3X, verified by sequencing, and expressed in *Escherichia coli*.

Figures 5B, 5C:
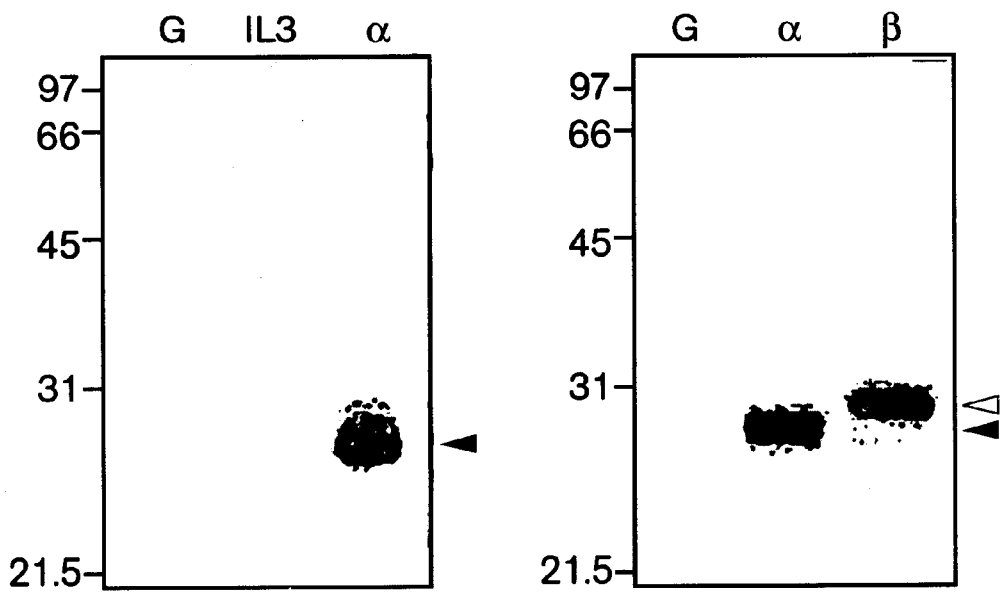
FIG. 5B is an autoradiograph showing in vitro phosphorylated GST-fusion peptides.
FIG. 5C is an autoradiograph showing in vitro phosphorylated GST-fusion peptides.

Purified fusion proteins (recombinant GST protein (G), the GST-TXA$_2$ receptor third cytoplasmic loop (iL3), or the GST-TXA$_2$ receptor tail sequence fusion protein corresponding to the α or β isoforms of the TXA$_2$ receptor, α and β, respectively) were introduced into a kinase reaction mixture containing 0.1 mM [γ-$^{32}$P]ATP and nanomolar concentrations of purified G kinase. For all in vitro phosphorylation studies, G kinase was prepared and characterized as reported (Cornwell, T. L. et al., 1989, *J. Biol. Chem.* 264:1146–1155). Proteins were quantitated by Bradford assay and on Coomassie-stained gels, and the same input concentrations of protein were used for the various peptides. FIGS. 5B and 5C represent two different experiments. The reactions were resolved on 10% SDS/PAGE gels to generate the autoradiographs shown. FIG. 5C: the dark arrowhead denotes the TXA$_2$ α carboxyl-terminal fusion protein; the open arrowhead denotes the TXA$_2$ β carboxyl-terminal fusion protein. One of three similar experiments is shown in each case. Native GST protein (G, left and right panels) was not phosphorylated in these studies, nor was the peptide derived from the third intracytoplasmic loop of the TXA$_2$ receptor phosphorylated (iL3, left panel), even when concentrations of these two fusion proteins 5–10 fold higher than those of the carboxyl-terminal peptide-derived fusion proteins were used. By contrast, physiologic concentrations of G kinase (8 nM) markedly catalyzed the phosphorylation of the fusion peptide corresponding to the cytoplasmic tail of the TXA$_2$ receptor α (FIGS. 5B and 5C). Phosphorylation of the α receptor carboxyl-terminal protein was dose-dependent and maximal at a G kinase concentration of approximately 40 nM. In separate studies, peptide corresponding to the cytoplasmic tail of the TXA$_2$ receptor β also was phosphorylated using G kinase (FIG. 5C, lane β). The level of phosphorylation of the α and β isoforms of the TXA$_2$ receptor carboxyl termini was quite similar in this assay, although the β form has 15 more serine/threonine residues than the α form available for phosphorylation.

EXAMPLE 4

Inhibition of Thrombin Receptor-mediated Vascular Smooth Muscle Cell Activation

Figure 6A:
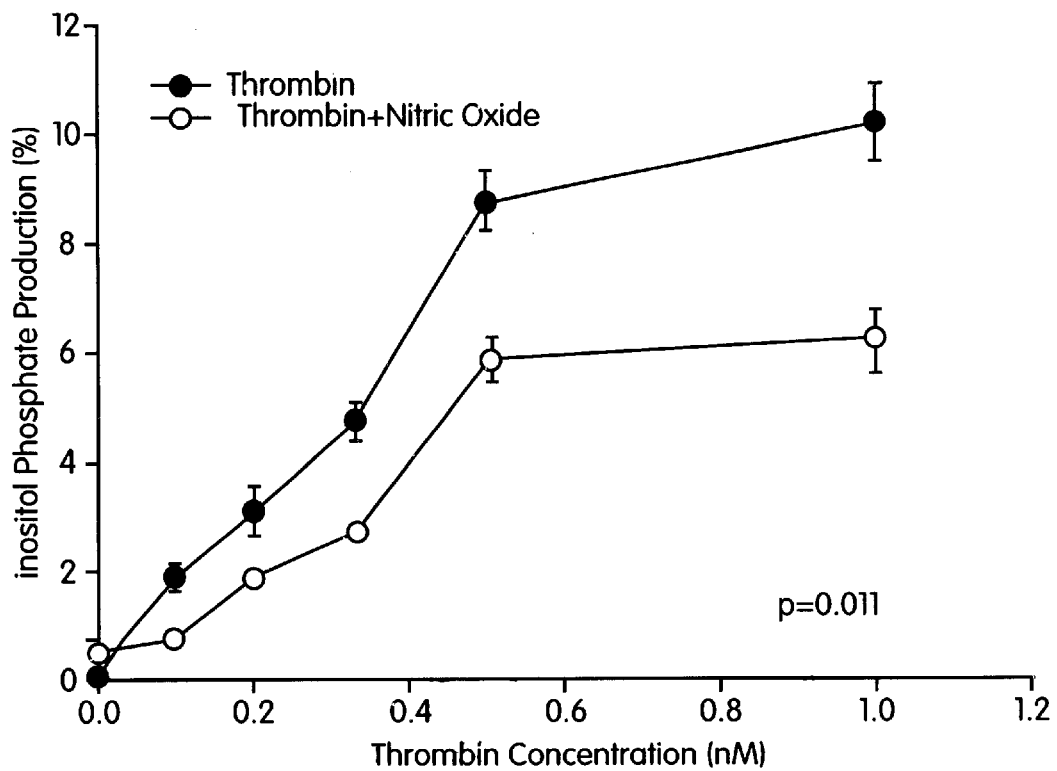
FIG. 6A is a graph showing inhibition of thrombin receptor-mediated vascular smooth muscle cell activation by nitric oxide.
Figure 6B:
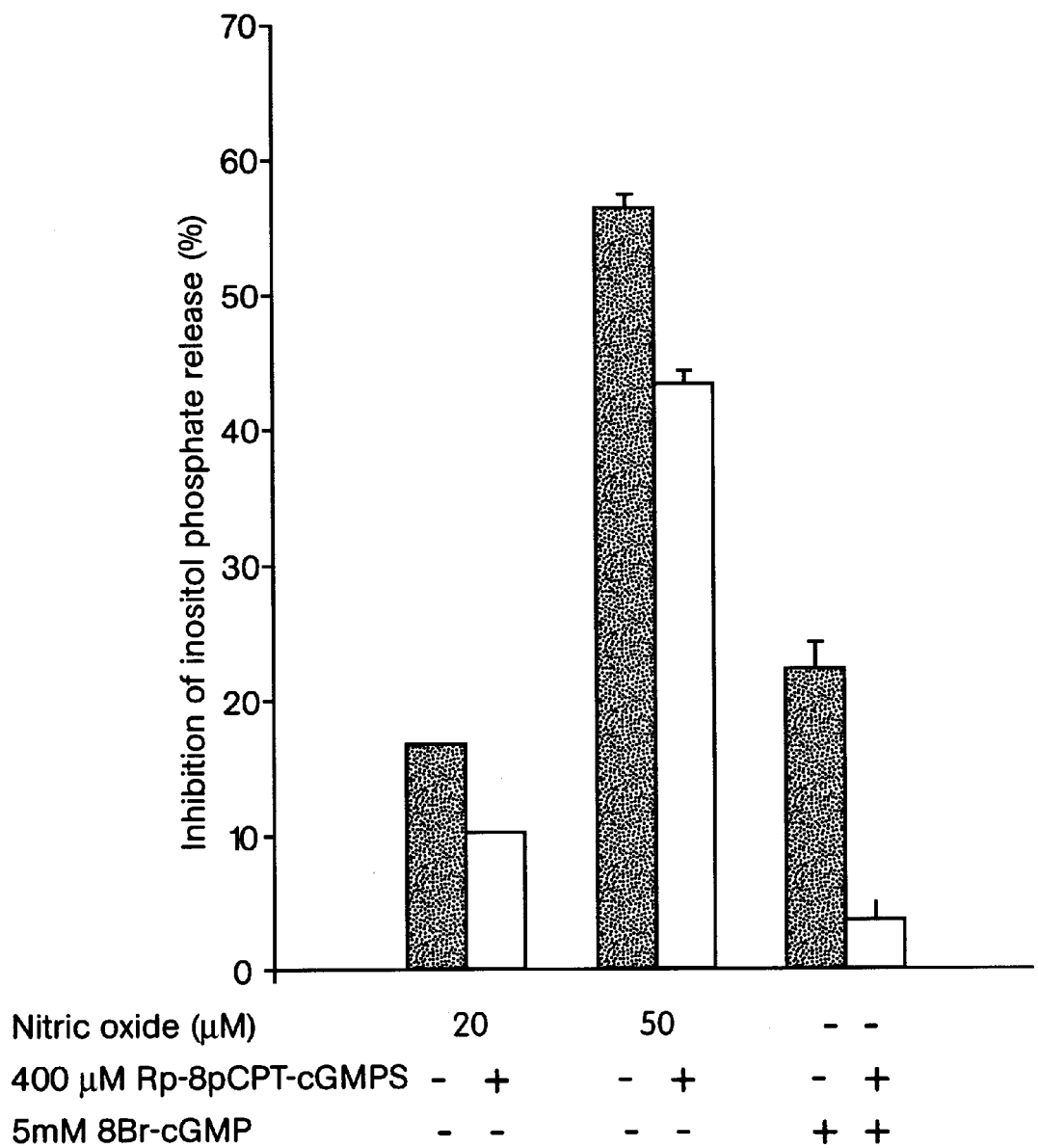
FIG. 6B is a graph showing inhibition of thrombin receptor-mediated vascular smooth muscle cell activation by nitric oxide and cyclic GMP. Reversal of this effect by inhibition by G kinase.
Figure 6C:
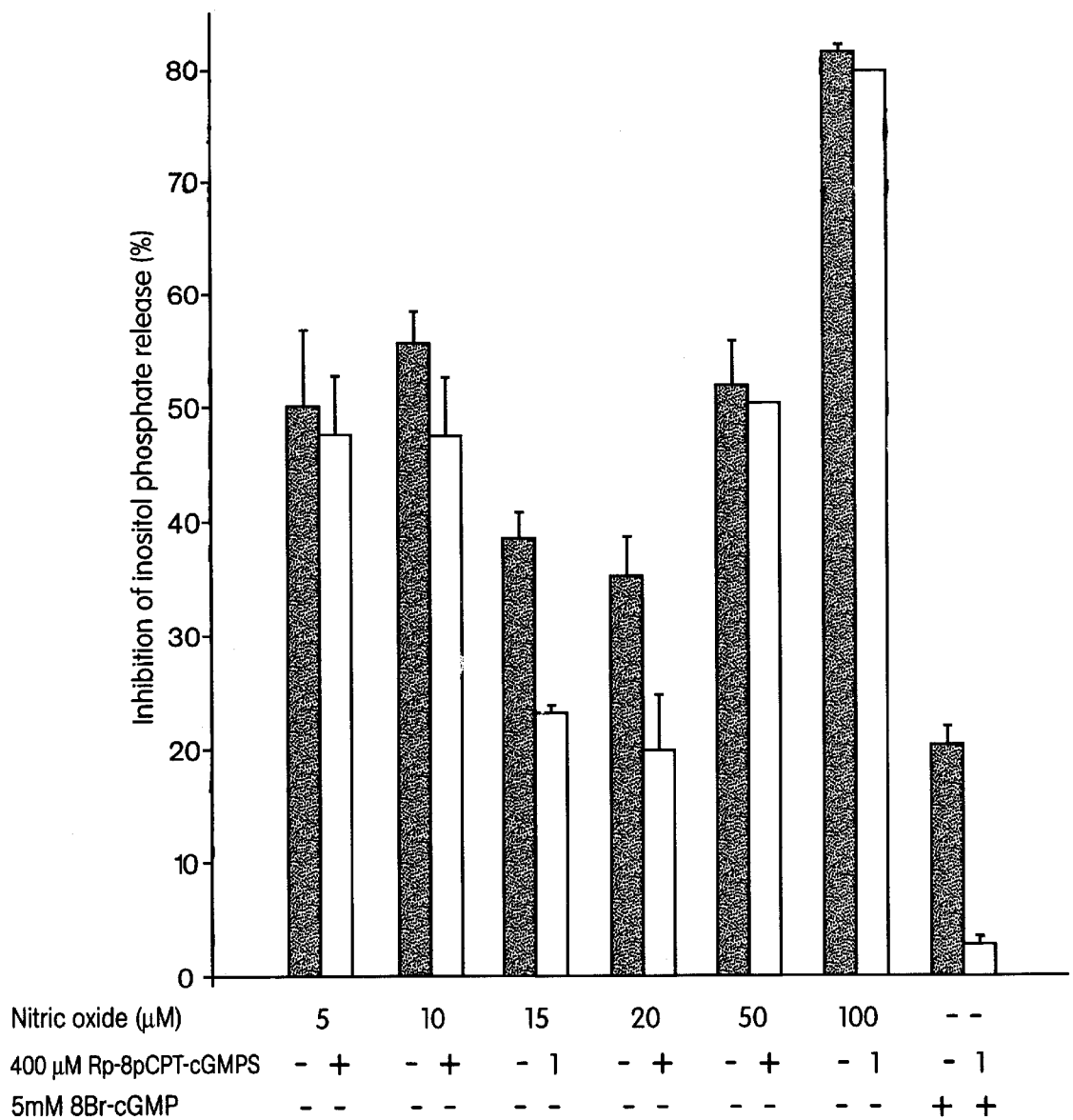
FIG. 6C is a graph showing inhibition of thrombin receptor-mediated vascular smooth muscle cell activation by nitric oxide and cyclic GMP. Reversal of this effect by inhibition by G kinase. Further dose response.

The activation of vascular smooth muscle cells by thrombin receptor is inhibited by nitric oxide (FIG. 6A). FIG. 6B shows inhibition of thrombin receptor-mediated vascular smooth muscle cell activation by nitric oxide and cyclic GMP. This effect is reversed by inhibition by G kinase. FIG. 6C shows a further dose response of the inhibition of thrombin receptor-mediated vascular smooth muscle cell activation by nitric oxide and cyclic GMP and of the reversal of this effect by inhibition by G kinase.

OTHER EMBODIMENTS

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

What is claimed is:

1. A method of assaying a test compound, said method comprising:
   (a) providing a system comprising
      (i) a G protein-coupled receptor-bearing cell,
      (ii) cyclic GMP or an analog thereof, and
      (iii) cyclic GMP-dependent protein kinase that phosphorylates said G-protein-coupled receptor;
   (b) contacting said test compound with said system; and
   (c) determining whether said test compound affects the phosphorylation of said G-protein-coupled receptor or cyclic GMP-dependent protein kinase phosphorylatable-fragment thereof.

2. The method of claim 1, wherein said cell is selected from the group consisting of platelets, human erythroleukemia cells, and vascular smooth muscle cells.

3. The method of claim 1, wherein said cell is genetically engineered to express said G protein-coupled receptor or cyclic GMP-dependent protein kinase phosphorylatable-fragment thereof.

4. A method of assaying a test compound, said method comprising:
(a) providing a system comprising
   (i) a G protein-coupled receptor-bearing cell preparation,
   (ii) cyclic GMP or an analog thereof, and
   (iii) cyclic GMP-dependent protein kinase that phosphorylates said G-protein-coupled receptor;
(b) contacting said test compound with said system; and
(c) determining whether said test compound affects the phosphorylation of said G-protein-coupled receptor or cyclic GMP-dependent protein kinase phosphorylatable-fragment thereof.

5. The method of claim 4, wherein said cell preparation is made from cells selected from the group consisting of platelets, human erythroleukemia cells, and vascular smooth muscle cells.

6. The methods of claims 1 or 4, wherein said method further comprises a G protein-coupled receptor agonist.

7. The method of claim 1, wherein said determining is done in vitro.

8. The method of claim 1, wherein said determining is done in vivo.

9. The method of claims 1 or 4, wherein said determining comprises measuring GTPase activity.

10. The method of claims 1 or 4, wherein said G-protein-coupled receptor is selected from the group consisting of thromboxane receptors, thrombin receptors, serotonin receptors, purinergic receptors, adrenergic receptors, bradykinin receptors, angiotensin receptors, cAMP receptors, dopamine receptors, muscarinic receptors, opioid receptors, and opsin receptors.

11. The method of claim 1 or 4, wherein said determining further comprises determining whether said test compound affects the activation of said cell.

* * * * *